(12) United States Patent
Scetta

(10) Patent No.: US 9,789,192 B2
(45) Date of Patent: Oct. 17, 2017

(54) OIL-BASED PHARMACEUTICAL COMPOSITION FOR THE TREATMENT OF GASTROINTESTINAL DISEASES

(71) Applicant: Gruppo Farmaimpresa S.r.l., Brescia BS (IT)

(72) Inventor: Daniele Scetta, Poggiomarino NA (IT)

(73) Assignee: Gruppo Farmaimpresa S.r.l., Brescia BS (IT)

( * ) Notice: Subject to any disclaimer, the term of this patent is extended or adjusted under 35 U.S.C. 154(b) by 0 days.

(21) Appl. No.: 14/376,905

(22) PCT Filed: Feb. 13, 2013

(86) PCT No.: PCT/IB2013/051159
§ 371 (c)(1),
(2) Date: Aug. 6, 2014

(87) PCT Pub. No.: WO2013/121354
PCT Pub. Date: Aug. 22, 2013

(65) Prior Publication Data
US 2015/0010511 A1    Jan. 8, 2015

(30) Foreign Application Priority Data

Feb. 13, 2012  (IT) .............................. NA2012A0005

(51) Int. Cl.
| | |
|---|---|
| *A61K 35/74* | (2015.01) |
| *A61K 36/06* | (2006.01) |
| *A61K 31/22* | (2006.01) |
| *A61K 47/44* | (2017.01) |
| *A61K 33/00* | (2006.01) |
| *A61K 31/695* | (2006.01) |
| *A61K 31/355* | (2006.01) |
| *A61K 9/08* | (2006.01) |
| *A61K 45/06* | (2006.01) |
| *A61K 47/24* | (2006.01) |
| *A61K 31/07* | (2006.01) |
| *A61K 31/122* | (2006.01) |
| *A61K 35/741* | (2015.01) |
| *A61K 35/00* | (2006.01) |

(52) U.S. Cl.
CPC ................ *A61K 47/44* (2013.01); *A61K 9/08* (2013.01); *A61K 31/07* (2013.01); *A61K 31/122* (2013.01); *A61K 31/355* (2013.01); *A61K 31/695* (2013.01); *A61K 33/00* (2013.01); *A61K 35/741* (2013.01); *A61K 36/06* (2013.01); *A61K 45/06* (2013.01); *A61K 47/24* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 3,767,794 A | * | 10/1973 | McVean ................. | A61K 9/145 424/499 |
| 4,514,319 A | * | 4/1985 | Kulkarni ............ | B01D 19/0409 516/117 |
| 2005/0215529 A1 | * | 9/2005 | Holoshitz et al. ............ | 514/102 |
| 2008/0102186 A1 | * | 5/2008 | Perlman ........................ | 426/601 |

FOREIGN PATENT DOCUMENTS

| | | |
|---|---|---|
| EP | 1468677 A2 | 10/2004 |
| WO | 99/63986 A1 | 12/1999 |
| WO | 03/026678 A1 | 4/2003 |
| WO | 2004/082669 A2 | 9/2004 |
| WO | 2012/130351 A1 | 10/2012 |

OTHER PUBLICATIONS

Dow Corning, Antifoams and Antifoam Emulsions Product Sheet, 18-19, 2005.*
Vinik, Al; et al; "Evidence for Histamine H1 and H2 Receptors in Guinea-Pig Oxyntic Cells" The Journal of Pharmacology and Experimental Therapeutics, 227, 115-121, 1983.*
Russian Office Action for Corresponding Russian Patent Application No. 2014137178 Dated Sep. 13, 2016. (9 Pages).
European Office Action for Corresponding European Patent Application No. 13713534.9-1460 Dated Oct. 11, 2016. (4 Pages).
Roberts et al, "Methyl Polysiloxane in Postoperative Gas Pains", JAMA, 1963, vol. 183, No. 7, pp. 595-597.
Author Abu Bakr Mohammad.Bin Zakariyya Al-Razi Title of publication—Kitaab-al-Haawi-fil-Tibb. vol. V Page(s) being submitted—04(p. No. 04-07) (Ref.pg. No. of publication:110 ) Publication Date—1979 AD Publisher—Dayerah-al- Ma'aarif Usmania Place of Publication—Hyderabad, India.†
Author Mohammad Najmul Ghani Khan Title of publication—Khazaain-al-Advia. vol. II Page(s) being submitted—4 (pg. No. 08-12) (Ref.pg. No. of publication:421 ) Publication Date—1911 AD Publisher—Nadeem Yunus Printer / Sheikh Mohd Basheer & Sons Place of Publication—Lahore.†
Author Mowaffaq Al- Din Abu Mansoor Ali Al- Harvi Title of publication—Al-Abnia-'an-Haqaayiq-al-Advia Page(s) being submitted—05 (p. No. 13-17) (Ref.pg. No. of publication:293 ) Publication Date—1992 AD Publisher—Tehran Place of Publication—Iran, India.†

* cited by examiner
† cited by third party

*Primary Examiner* — David Berke-Schlessel
(74) *Attorney, Agent, or Firm* — Lucas & Mercanti, LLP

(57) ABSTRACT

The present invention relates to a composition for oral use in the treatment of gastrointestinal pathologies comprising silicone antifoaming agents in an oily solvent medium, wherein the concentration of said silicone antifoaming agents is between 0.1% and 80% by weight.

5 Claims, 4 Drawing Sheets

OIL-BASED PHARMACEUTICAL COMPOSITION FOR THE TREATMENT OF GASTROINTESTINAL DISEASES

CROSS-REFERENCE TO RELATED APPLICATIONS

This application is a 371 of PCT/IB2013/051159, filed Feb. 13, 2013, which claims the benefit of Italian Patent Application No. NA2012A000005, filed Feb. 13, 2012, the contents of each of which are incorporated herein by reference.

FIELD OF THE INVENTION

The present invention relates to the field of products for oral use and in particular to an oily composition incorporating an antifoaming agent employable for the treatment of gastrointestinal disorders or, by way of example, in case of dyspeptic disorders, when the reduction of the time of gastric emptying is required, for treating *H. pylori*, in case of irritable bowel syndrome (IBS), as well as in case of gas, bloating, flatulence, and in the treatment of intestinal colic, especially in children and infants.

Said association allows the relief of abdominal symptoms through gastrointestinal wall protection and easing of the disturbance caused by the increased air pressure in the intestine.

SUMMARY OF THE INVENTION

It is therefore an object of the present invention an oily composition comprising a silicone antifoaming agent, preferably simethicone.

In this composition, thickening agents, dispersible solids (powders), nourishing substances, anti-diarrheal agents, enzymes, immunostimulating agents, antacid substances that may act directly or indirectly, substances inhibiting the activity of Pylori type microorganisms, antiradical agents such as, for example, vitamin A, vitamin E and coenzyme Q can be optionally added, in order to make it more effective or more palatable, either during manufacture or shortly before use.

Prebiotic substances may be also added such as, by way of example, inulin, fructooligosaccharides (FOS), oligofructoses, galacto-oligosaccharides, lactulose, oligosaccharides and probiotic yeasts such as *Saccharomyces boulardii, Saccharomyces cerevisiae* or bacteria belonging, by way of example, to the species of *Bifidobacterium, Enterococcus* and *Strepterococcus*.

Optional variants of the above described composition are intended to make the invention more efficient in specific cases such as gastric ulcers, colic with diarrhea caused by antibiotics etc.

The advantages produced by a composition of simethicone dispersed in an oily phase (preferably consisting of olive oil), compared to the formulations of simethicone in an aqueous phase that are currently on the market, are manifold:

1) better dispersion of simethicone in the composition according to the invention compared to products made with simethicone in an aqueous base.

2) the absence of preservatives in the composition according to the invention, unlike those currently on the market.

3) greater structural similarity between milk and the composition according to the invention, compared to those currently commercially available;

4) increased activity of the composition according to the invention compared to those in aqueous phase that are currently on the market.

BRIEF DESCRIPTION OF THE DRAWINGS

Advantages and characteristics according to the present invention will become apparent to those skilled in the art from the following detailed description and non-limiting description of an embodiment thereof with reference to the accompanying drawings in which.

DETAILED DESCRIPTION OF THE INVENTION

Figure 1:
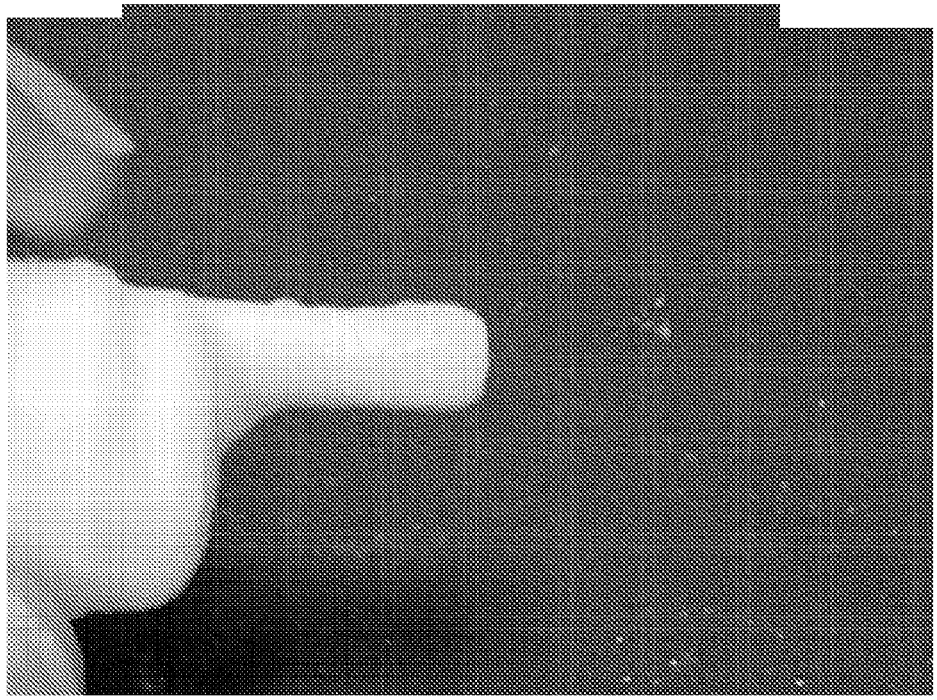
FIG. 1 is a photograph of a dropper of the product Mylicon (batch fc158 expiration January 2014) in which the presence of lumps in suspension is apparent.
Figure 2:
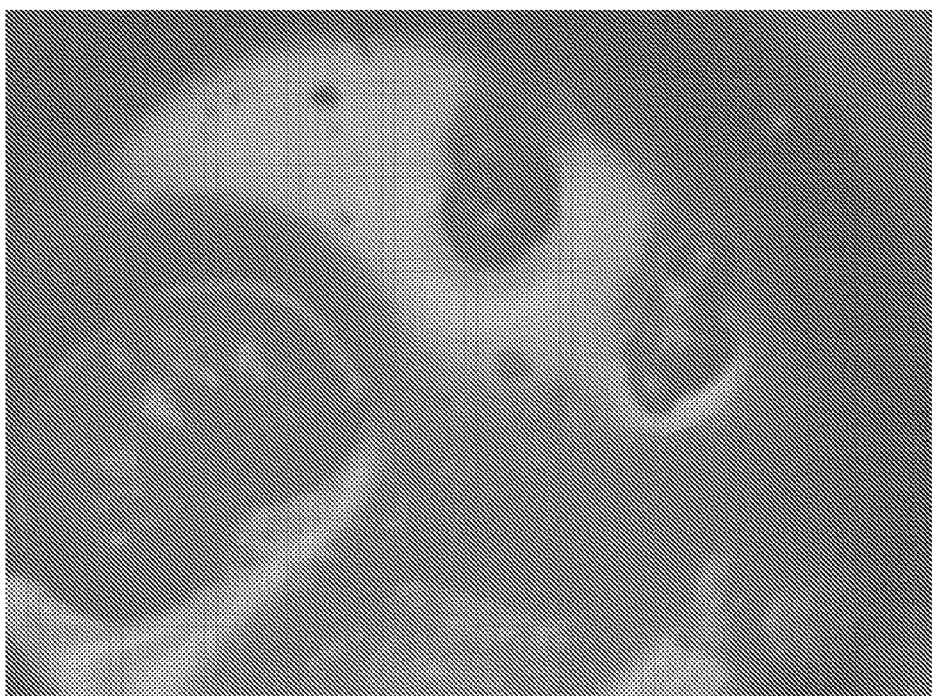
FIG. 2 is a photograph of the liquid part of the product Mylicon (batch fc158 expiration January 2014), previously subjected to vigorous stirring for five minutes, with the presence of white lumps in adhesion.
Figure 3:
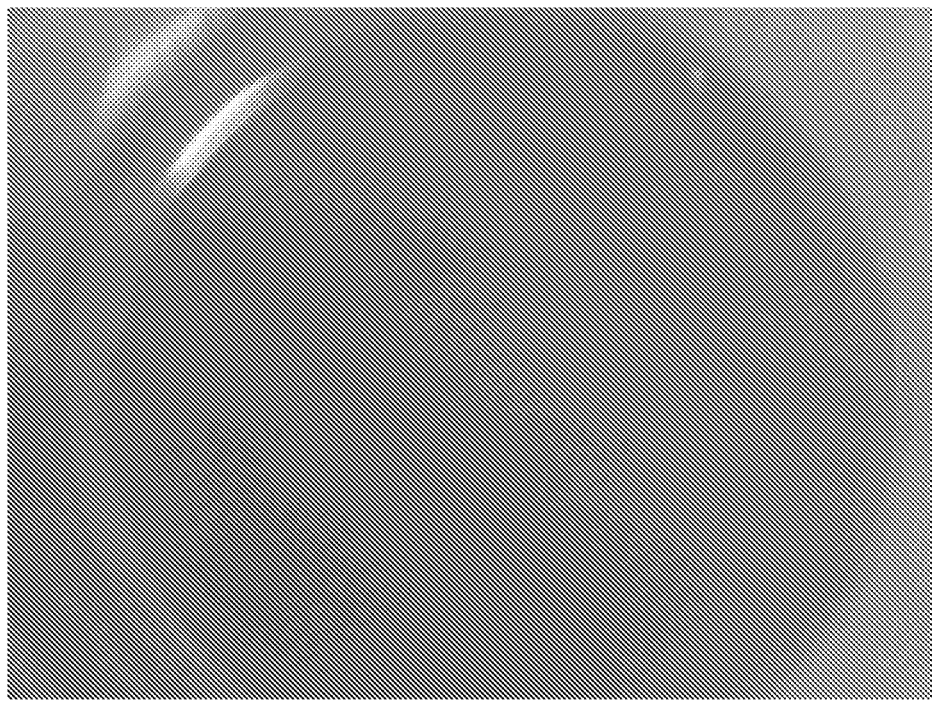
FIGS. 3 and 4 represent photographs of the product object of the invention at the end of the period of accelerated stability in an oven at 40 for three months, in which it is apparent the absence of lumps both in the preparation (FIG. 2) and in the dropper (FIG. 3)
Figure 4:
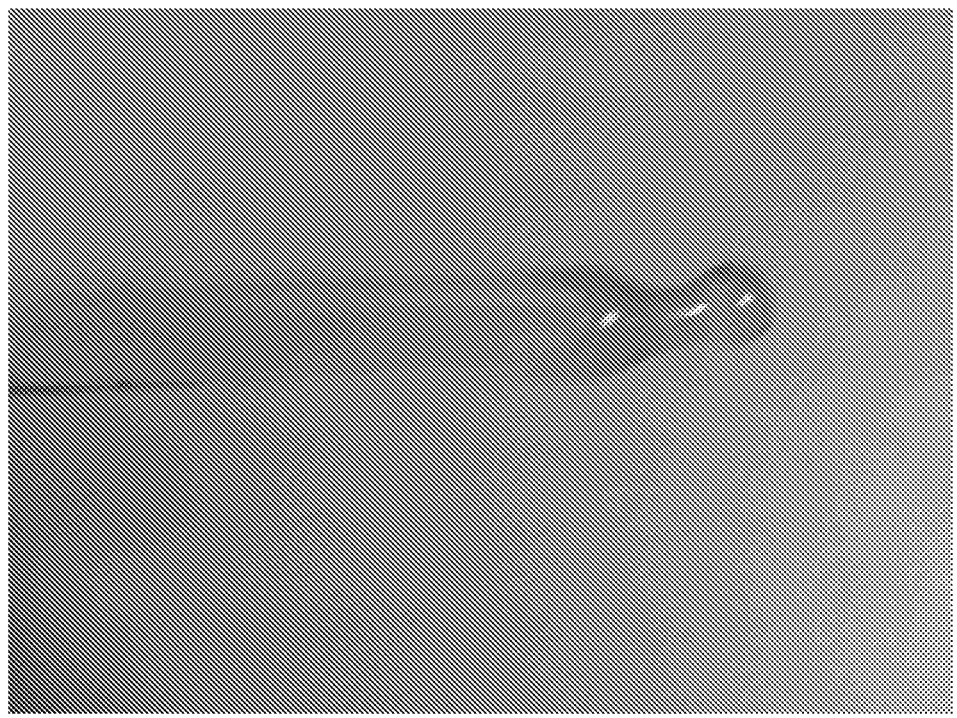

These advantages are illustrated below:

1. Better dispersion of simethicone in the composition according to the invention compared to products made with simethicone in an aqueous base.

The better dispersion of simethicone in the preparation allows:

a lower agitation by the user of the composition.
a better homogeneity of the composition and, therefore, a more easy and accurate administration of the antifoam product (simethicone).
A more fluent and easy administration of the composition as it is more homogeneous and free of any corpuscles.

This is due to the fact that the oil used (for example olive oil), thanks to its chemical and physical properties, is more compatible compared to water with the structure of the highly hydrophobic and lipophilic simethicone; such better compatibility produces an improvement in the pharmaceutical form of the composition. In fact, in the devices currently on the market, in which the simethicone, lipophilic molecule, is dispersed in a solvent highly hydrophilic such as water, a dispersion or an emulsion is obtained, where the molecules of simethicone tend to aggregate together. In some formulations, white lumps can also be present both in the preparation and adhered to the walls of the dropper tip; these lumps may, in certain cases, make it difficult to drip the preparation from its container so that it is necessary to energically shake the container to disperse simethicone in the aqueous medium and let it come out.

With the composition according to the present invention, which includes as a dispersing agent olive oil, that is highly lipophilic and therefore chemically akin to simethicone, a chemically homogeneous system is obtained and therefore a complete solubilization of simethicone in an oily medium.

Then, the product according to the invention, until the end of its life cycle, will not form the characteristic lumps that are present in products based on simethicone, in aqueous phase or on the inner walls of the dropper, as shown in FIGS. 1, 2, 3, 4.

2. Absence of preservatives in the composition according to of the invention, unlike those currently on the market.

All simethicone products in aqueous phase that are currently on the market include the presence of one or more preservatives such as, for example, sodium benzoate, potassium sorbate; since the presence of water generates the possibility of bacterial and fungal proliferation.

The composition according to the present invention, being free of water does not allow the activities and the proliferation of microorganisms, thus allowing the absence of antimicrobial preservatives that are possibly sensitising.

3. Greater structural similarity between milk and the composition according to the present invention, compared to those currently commercially available.

The simethicone based products are often administered to infants in order to alleviate the symptoms of colics and swollen abdomen; in these patients, often, simethicone based products are dispersed into some (often maternal) milk in order to facilitate the administration.

Besides the fact that it is not advisable to give water to infants during the first six months of life, olive oil has a high similarity in terms of composition, with the breast milk, so that it is highly digestible in infants and is an essential food for the proper development of the child.

4. Increased activity of the composition according to the present invention with respect to those currently commercially available The greater activity of the composition according to the present invention compared to those currently on the market is due to the synergy of action between olive oil and simethicone.

The composition according to the present invention therefore comprises silicone antifoaming agents in an oily medium. Preferably these silicone antifoaming agents are simethicone. Preferably, such an oily medium consists of olive oil.

The amount of simethicone or other silicone antifoaming agents is between 0.1 and 80% by weight, more preferably between 0.5% and 15% by weight, still more preferably between 3 and 12% by weight, relative to the total weight of the composition according to the present invention.

Preferably, the composition according to the present invention also comprises silicon dioxide, in addition to simethicone and olive oil.

The concentration by weight of silicon dioxide with respect to the total weight of the composition is between 0.01% and 10% by weight, preferably between 0.1% and 5%.

According to a preferred embodiment of the invention, the composition comprises simethicone in an amount comprised between 6 and 8%, and silicon dioxide in an amount comprised between 1.5% and 3%, and olive oil as an oily solvent medium.

The composition of the present invention has the form of liquid solution for oral administration.

Optionally, the composition according to the present invention may comprise radical scavenger such as fat-soluble vitamins.

Optionally the composition according to the present invention may comprise solid substances (powders) dispersible in order to increase the activity of the product.

Optionally the composition according to the present invention can include prebiotics and probiotics.

Optionally the composition according to the present invention may comprise enzymatic, immunostimulant, gastroprotective substances, substances inhibiting the activity of the microorganisms of the species *pylori*.

All the mentioned optional substances can be added into the product during the production phase or at the time of use.

According to a further aspect thereof, the present invention relates to a kit for the preparation of a composition containing simethicone, an oily solvent medium, and possibly silicon dioxide as well as possibly one or more substances selected from enzymes, antacid substances having direct or indirect action, thickeners, dispersible solid substances (powders), prebiotic substances, immunostimulating substances, antidiarrhoeal substances, nutrients, substances having inhibitory activity of microorganisms of the pylory type, gastroprotective acting substances, free radical scavenging agents, probiotics belonging to the families of yeasts and bacteria, in which these substances are contained in a separate unit, for example a sachet or a vial, and are to be dispersed in the oily solvent medium containing the simethicone shortly before the administration to the end user.

According to a preferred embodiment, the composition according to the present invention, contains per 100 ml of final product:

MATERIALS SOLUTION quantity %
Olive oil 87.880%
Simethicone USP 7.500%
Vitamin A Palmitate 1700000 u.i 0.120%
Vitamin E Acetate 3.000%
Coenzyme Q10 0.002%
Micronized silica (silicon dioxide) 1.500%

According to a further preferred embodiment, the composition according to the present invention contains, per 100 ml of final product:

MATERIALS SOLUTION quantity %
Olive oil 90.30%
Simethicone USP 6.66%
Vitamin A Palmitate 1700000 u.i 0.24%
Vitamin E acetate 1.20%
Coenzyme Q10 0.10%
Micronized silica (silicon dioxide) 1.500%

Tests of accelerated stability at three months were also performed on these compositions, with:
1. Determination of acidity and peroxide index
2. Determination of bacteria, molds, yeasts and pathogens as required by Italian Official Pharmacopoeia XII ed.

The stability, tested at room temperature and at a temperature higher than 40° C., showed the stability of the compositions.

Tests for acute toxicity were also made on the compositions, which showed the harmlessness of the same.

The composition according to the present invention is directed to the treatment of disorders of intestinal function. The active ingredient is simethicone (activated methylpolysiloxane), a chemically inert polymer of methylsiloxane. The mechanism of action of these products is mechanical and physical and resides in the ability of the products to favor the aggregation of gas bubbles trapped in the gastrointestinal tract and the formation of free gas that is more easily eliminated from the mouth or anus. In addition to simethicone, for the activity of the product, the presence of olive oil is important, that allows optimal dispersion and administration of simethicone and also enhances the activity.

Figure 5:
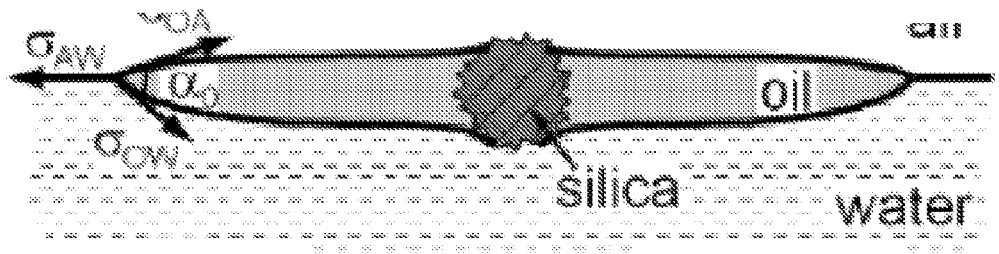
FIG. 5 is a drawing that shows the forces of surface tension in a system air/oil/water and hydrophobic particles.

The possible addition of silicon dioxide (micronized silica) seems responsible for an immediate reduction of the effect of air bubbles. According N. A. Denkov is possible to distinguish a mechanism of action of the breaking of the bubbles fast (called "Fast") which is expressed in about 10 seconds, typical of the silica particles, compared to a slow effect (called "Slow"), typical of simethicone, which is carried out between 5 and 10 minutes. The effect of breaking of the bubbles either by solid particles that of the oil droplets is closely related to their hydrophobicity, and is quantified based on the value of the contact angle of the three phases: solid-water-air (see FIG. 5).

Figure 6:
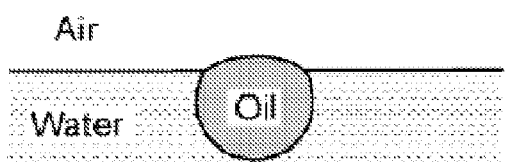
FIG. 6 is a drawing that shows the mechanism of "bridge-dewetting" type breakage of the foam caused by the solid particles hydrophobic.
Figure 6:
Figure 6:
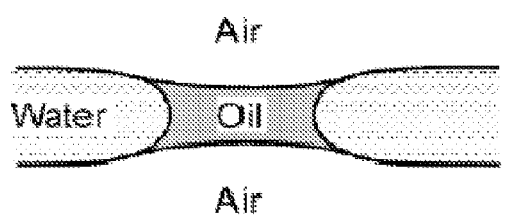
Figure 6:
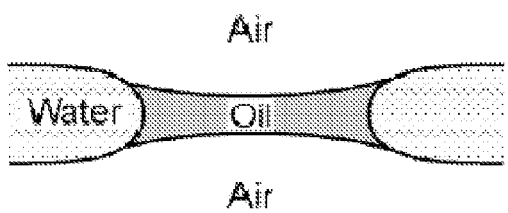
Figure 6:
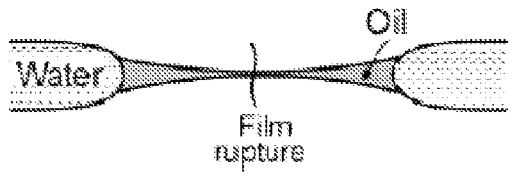

It has been experimentally and theoretically demonstrated that hydrophobic solid particles can break the film composed of the bubbles, hereinafter called foam through the so-called "bridge-dewetting" mechanism. This mechanism implies that, in the first place, the solid particle to come in contact with the two opposite surfaces of the foam film, forming a solid bridge between them. If the particle is sufficiently hydrophobic, it is not wetted by the liquid, bringing the contact lines of the three phases Air/Particle/Water in contact with each other, thus resulting in the formation of bridges between the two layers that generate the bubble and the resulting coalescence. This behavior is identified with the so-called "Fast" mechanism that gives rise to the breakage of the bubbles (see FIG. 6).

Figure 7:
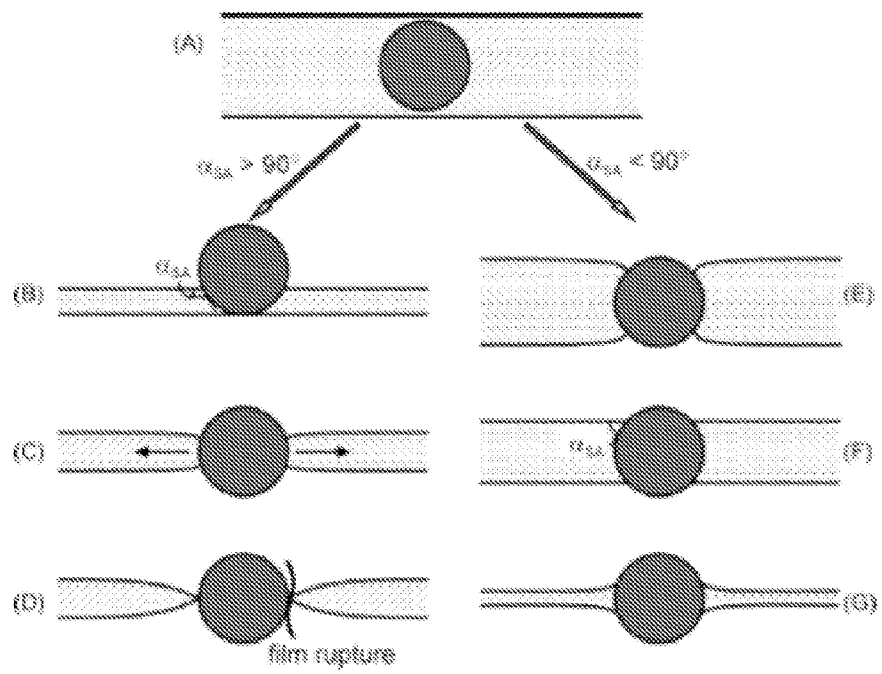
FIG. 7 is a drawing representing the mechanism of "bridge-stretching"-type breakage of the foam caused by oily particles.

The mechanism of antifoaming action of the oily particles is explained according to a different model. In fact, in addition to the "bridging-dewetting" mechanism as applied to solid particles, in the case of a deformable particle such as the oil particle, there are two possibilities, ie that it behaves in the same way with respect to a solid particle, or that it acts according to the "bridging-stretching" mechanism as exemplified in FIG. 7.

Figure 8:
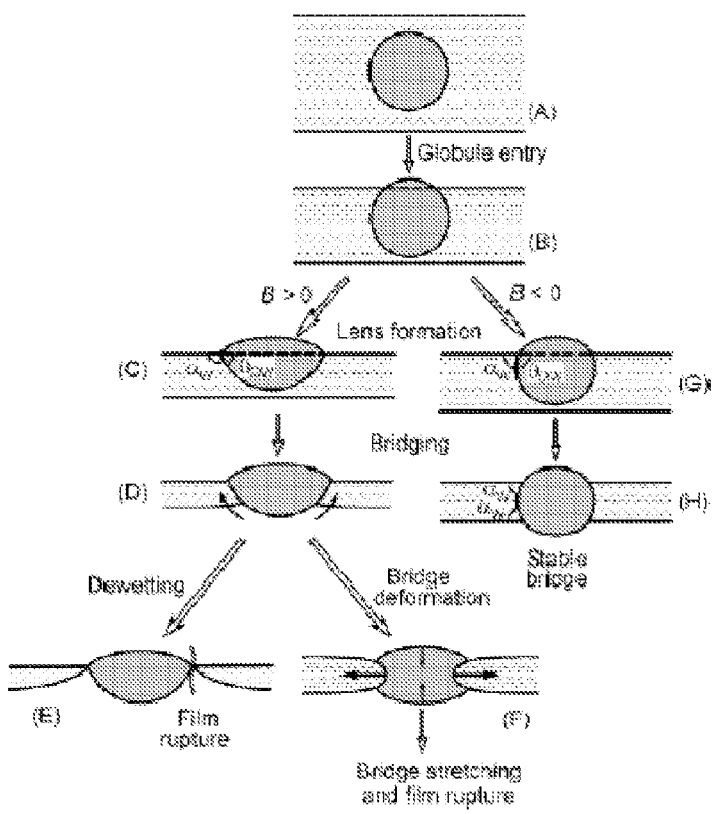
FIG. 8 is a drawing representing the mechanism of combined "bridge-dewetting" and "bridge-stretching"-type breakage of the foam as applied to oily particles.

Then, for an oil particle the mechanism of action can be explained by using the two above described models together (see FIG. 8).

Considering the difficulty to predict on theoretical grounds the defoaming effect, or rupture of the air bubbles of a preparation (since the overall effect takes account of the different mechanisms of action), mathematical models have been developed, aimed to predict the effect of antifoam products based on the values of surface tension of air/water σAW, Oil/Water σOW and Oil/Air σOA.

Garrett in his model defines a "bridging" coefficient B that identifies the ability of a product to form bridges between the two layers which form the walls of the bubbles and responsible for the coalescence of the same.

The parameter B is directly related to the values of the surface tension Air/Water σAW, Oil/Water σOW and Oil/Air σOA that are related to each other by the following relation:

$$B = \sigma AW^2 + \sigma OW^2 - \sigma OA^2$$

In this model for the values of B>0, the behavior of the oil globule is to be considered destabilizing for the foam bubble, then the product will be active as anti-foam, and for values of B<0 a stabilizing effect is expected towards the bubble, and then the product will be not active as defoamer.

From the relation between the coefficient of "bridging" B and the surface tensions, it is immediate that low values of surface tension Oil/Air (σOA) correspond to best antifoaming ability.

EXAMPLES

Given the circumstances, the measurement of the surface tension of two preparations has been carried out:

a composition A according to the present invention, comprising simethicone 6.66% in olive oil; and the commercial product Mylicon comprising simethicone 6.66% in aqueous solution with citric acid monohydrate, sodium citrate; methylhydroxypropylcellulose; carboxypolymethylene; saccharin; sodium benzoate; sorbic acid; sodium bicarbonate; essence of raspberry; concentrated essence of vanilla.

As measuring system, a ring system of measurement with dynamometer according to the Du Nouy method was used.

The algorithm applied for calculating the value of was:

$$\tau = \frac{F2 - F1}{4\pi r}$$

τ=surface tension (σOA)
F2=weight force at the beginning of experiment
F1=weight force at the time of detachment of the ring from the liquid surface
R=radius of the metal ring As a first test, system calibration was carried out by measuring the surface tension of distilled water in environmental condition next to standard conditions T=25° C.; P=atmospheric pressure. The value obtained from the three measurements has resulted in an average value of 7.11 g/m, very close to the theoretical value of distilled water, i.e. 7.42 g/m.

With the thus calibrated system, determination of the values of surface tension has been carried out in triplicate for the product object of the present invention as defined above and Mylicon (commercial product); the obtained results are shown below:

| Product | Size 1 | Size 2 | Size 3 | Average |
|---|---|---|---|---|
| Comp. simethicone 6.66% by weight in olive oil | 1.30 g/m | 1.24 g/m | 1.36 g/m | 1.3 g/m |
| Mylicon (simethicone 6.66% in water) | 1.62 g/m | 1.56 g/m | 1.56 g/m | 1.58 g/m |

These results show improved activity of the composition according to the invention compared to the commercial composition that has a known activity in lowering the surface tension, a necessary condition for the activity of the preparation in breaking the air bubbles; such activity was shown experimentally by comparing the following compositions in a further test:

composition B according to the invention (including oil and simethicone 6.66% by weight)

composition C according to the invention (comprising oil and simethicone 6.66% by weight and silicon dioxide and 1.5% by weight)

Mylicon (commercial preparation having the above described composition)

Composition TN, prepared in the laboratory, comprising simethicone 6.66% by weight in water.

Composition C according to the invention has been considered in the experiment in order to demonstrate that the base product (oil and simethicone) can still be improved by adding silicon derivatives and solid particles that are dispersible in oil.

The composition TN based on simethicone and water has been inserted in the experiment in order to compare the product according to the invention with a standard just made product (simethicone in water).

Below, the details of the experiment are given, that was carried out by taking into account the publications of the American Standard Test Methods Int, which has published a variety of methods for the direct measurement of the antifoam effect making use of different model systems.

The method E2407-04 was defined as useful by the same ASTM Int for the testing of liquid antifoaming agents, such as silicone emulsions or organic antifoam agents. The method is also considered valid to determine the relative efficacy of an antifoam agent with respect to another. The foaming agent used in the test is Sodium Lauryl Sulfate (SLES) at the concentration of 0.1%, prepared in water having hardness of 342 ppm expressed in French degrees. The method involves the formation of foam under standard conditions controlled by means of a "blender" to the maximum rotational speed of 22,000 rpm.

For the measurement of the relative antifoam capacity, 500 mg of each of the compositions B, C, TN and Mylicon were added in 250 ml of foam solution used for the test (Sodium Lauryl Sulfate (SLES) 0.1%, in water at a hardness of 342 ppm expressed in French degrees.). The measurements were conducted in triplicate.

The results are expressed in % reduction of the foam by applying the equation below:

$$fr\ \% = 100(ifv - efv)/ifv$$

fr %=foam reduction percentage
ifv=initial foam volume
efv=final foam volume

The reported results are the average of 3 absolute determinations; the deviation of the average from the more extreme results does not exceed 20%

| Composition | Average reduction of foam fr % |
|---|---|
| Composition B | 50 |
| Composition C | 80 |
| Mylicon | 28 |
| Composition TN | 29 |

The above mentioned values demonstrate the remarkably higher activity in breaking the air bubbles of the product according to the invention compared to products containing simethicone in an aqueous base.

In addition to the above experiment it was decided to experimentally determine the extent of the antifoam properties of the product object of the invention compared with the product Mylicon in a model system consisting of fresh whole milk (typical food of infants).

Due to the application of the products in the treatment of the effects of colic in the newborn during the first months of life and the fact that the milk (either breast milk or prepared industrial) at this stage of growth is virtually the only food, it was decided to repeat the measures provided by the method ASTM E2407-04 by using fresh whole milk, in place of SLES 0.1%, as foaming matrix. The obtained results are shown below; the results are expressed as % reduction of the foam using the equation below:

$$fr\ \% = 100(ifv - efv)/ifv$$

fr %=foam reduction percentage
ifv=initial foam volume
efv=final foam volume

| Composition | Fr % Measure 1 | Measure 2 | Measure 3 | Average |
|---|---|---|---|---|
| composition comprising 6.66% of simethicone in olive oil dispersed in a foam solution of fresh whole milk | 66.6% | 66.6% | 66.6% | 66.6% |
| Mylicon compr.6.66% simethicone in aqueous solution dispersed in a foam solution of fresh whole milk. | 33.3% | 33.3% | 33.3% | 33.3% |

The above experiments were carried out by the Chibilab certificate chemical\physical laboratory, to determine the chemical and physical measures in order to make a judgment supported by empirical data on the effectiveness as antifoam of the product according to the invention. It is assumed that the mechanism of operation of the preparations is based primarily on the ability of simethicone to reduce the diseases caused by the persistence of air in the gastrointestinal tract of the infant, through the mechanism of coalescence and elimination of air bubbles, as demonstrated by the current literature. Considering the qualified scientific sources and the implementation of effective methods of literature, the obtained measurements are considered as useful for this purpose.

From the collected data on the surface tension of the examined products, an oil/air surface tension value of the product according to the invention was shown to be lower than the value obtained in the same conditions for the product Mylicon.

The ASTM E 2407 test on the two products produced net results that allow the conclusion that the product of the invention shows an anti-foaming capacity about three times higher (fr %=80%) than the product Mylicon (fr %=28%). In addition, the empirical observation that when the product according to the invention is added to the foam system, there is a quick and obvious disappearance of the foam with a crackle effect, due to the rapid explosion of bubbles. Following the addition of the product according to the invention from the top on the foam matrix, there is a reduction in the volume of remaining individual bubbles. The mixture of foaming agent and defoamer has proven stable even after new shaking.

The product Mylicon also showed a defoaming effect, but to a lesser extent compared to the product according to the invention. Mylicon however did not show a clear reduction of the measurement of the size of the residual bubbles, as found instead for the product according to the invention. Finally, the tests conducted by the whole milk foam system, even if the differences were lower than in the SLES 0.1% experiment, has confirmed the higher antifoam capacity of the product according to the invention compared to Mylicon (fr % Composition comprising 6.66% of simethicone in olive oil=66.6% vs fr Mylicon %=33.3%) in the fresh whole milk model system.

Considered as a whole, these data prove that the foam reducing ability of the product according to the invention, found in several experimental models, is higher than that of the product Mylicon, which is a leader product in the market segment to which the invention refers.

Besides, the results of further tests are given below.

In the following table 1 row data on the defoaming activity are reported of different compositions according to the invention named RILEX ACE having formula:
Olive oil q.s. to 100 grams
Simethicone usp with different % w/w for each composition
Micronized silica (silicon dioxide) with different % w/w for each composition.

In the following table 1 row data on the defoaming activity are reported of different compositions according to the invention named RILEX ACE. Data were obtained by the test ASTM method E2407-04 (Reapproved in 2209). Tests were carried out using conditions described in the method and in the protocol P-12-001-ANFA of E&G Food Development Centre. The table reports the volume of liquid and foam contained in the blender cup after 30 s of blending of 250 mL of 0.1% sodium lauryl ether sulfate-SLES solution prepared in the condition described in the protocol P-12-001-ANFA. In the same table are reported the volumes of liquid and foam contained in the blender cup after addition of 500 mg of the product formulation and after 60 s of gentle mixing at 20% of the maximum power of the blender as described in the protocol P-12-001-ANFA.

TABLE 1

Row data of defoaming activity measured by ASTM method E2407-04.

| Composition | Test N° | Volume of liquid in ml | Volume of foam in ml | Volume of liquid in ml after addition of composition | Volume of foam in ml after addition of composition |
| --- | --- | --- | --- | --- | --- |
| Form A | 1 | 187.5 | 800 | 200 | 750 |
| Form AA | 26 | 193.75 | 800 | 206.25 | 362.5 |
| Form AB | 27 | 187.5 | 800 | 212.5 | 375 |
| Form AC | 28 | 187.5 | 800 | 212.5 | 375 |
| Form AD | 29 | 200 | 750 | 200 | 750 |
| Form AE | 30 | 187.5 | 800 | 200 | 650 |
| Form AF | 31 | 187.5 | 800 | 200 | 625 |
| Form AG | 33 | 200 | 800 | 200 | 375 |
| Form AH | 34 | 187.5 | 800 | 212.5 | 350 |
| Form AI | 35 | 187.5 | 800 | 212.5 | 350 |
| Form B | 2 | 200 | 800 | 200 | 750 |
| Form C | 3 | 200 | 800 | 200 | 700 |
| Form D | 4 | 200 | 800 | 200 | 700 |
| Form E | 5 | 200 | 800 | 200 | 650 |
| Form F | 6 | 200 | 750 | 225 | 400 |
| Form G | 7 | 200 | 800 | 225 | 400 |
| Form H | 8 | 200 | 800 | 200 | 800 |
| Form I | 9 | 187.5 | 800 | 200 | 750 |
| Form L | 10 | 200 | 750 | 200 | 750 |
| Form M | 11 | 187.5 | 800 | 200 | 800 |
| Form N | 12 | 187.5 | 800 | 200 | 750 |
| Form O | 13 | 187.5 | 800 | 200 | 675 |
| Form P | 14 | 187.5 | 800 | 200 | 600 |
| Form Q | 15 | 187.5 | 800 | 200 | 450 |
| Form R | 16 | 187.5 | 800 | 200 | 475 |
| Form S | 17 | 193.75 | 800 | 200 | 425 |
| Form T | 18 | 187.5 | 800 | 200 | 387.5 |
| Form U | 19 | 187.5 | 800 | 200 | 400 |
| Form V | 20 | 187.5 | 800 | 200 | 550 |
| Form Z | 21 | 187.5 | 800 | 200 | 450 |
| Form W | 24 | 187.5 | 800 | 200 | 425 |
| Form X | 22 | 187.5 | 800 | 200 | 700 |
| Form Y | 23 | 187.5 | 800 | 200 | 550 |

In the following table 2 test results were reported as % of foam reduction value for each RILEX ACE formulation tested. Data were obtained as described by the ASTM test method E2407-04 (Reapproved in 2209) and in the protocol P-12-001-ANFA of E&G Food Development Centre. The table reports the name of the formulation of RILEX ACE at different concentrations of Simethicone and Silice and different ratio together with the % of foam reduction value. The percentage of foam reduction was calculated as specified in the test ASTM method E2407-04 (Reapproved in 2209) and as reported in the protocol P-12-001-ANFA of E&G Food Development Centre.

TABLE 2

Results of percentage of foam reduction related to the composition of formulations tested

| # | Composition | % SIMETHICONE | % SILICA | % Foam reduction |
| --- | --- | --- | --- | --- |
| 1 | RILEX ACE FORM A | 0.66 | 0 | 10.2 |
| 2 | RILEX ACE FORM B | 2.60 | 0 | 8.33 |
| 3 | RILEX ACE FORM C | 4.60 | 0 | 16.67 |
| 4 | RILEX ACE FORM D | 6.60 | 0 | 16.67 |
| 5 | RILEX ACE FORM E | 8.80 | 0 | 25.00 |
| 6 | RILEX ACE FORM F | 11.00 | 0 | 68.18 |
| 7 | RILEX ACE FORM G | 13.20 | 0 | 70.83 |
| 8 | RILEX ACE FORM H | 0 | 0.15 | 0.00 |
| 9 | RILEX ACE FORM I | 0 | 0.35 | 10.20 |
| 10 | RILEX ACE FORM L | 0 | 0.70 | 0.00 |
| 11 | RILEX ACE FORM M | 0 | 1.50 | 2.04 |
| 12 | RILEX ACE FORM N | 0 | 3.00 | 10.20 |
| 13 | RILEX ACE FORM O | 0 | 9.00 | 22.45 |
| 14 | RILEX ACE FORM P | 0 | 15.00 | 34.69 |
| 15 | RILEX ACE FORM Q | 6.60 | 0.15 | 59.18 |
| 16 | RILEX ACE FORM R | 6.60 | 0.35 | 55.10 |
| 17 | RILEX ACE FORM S | 6.60 | 0.70 | 62.89 |
| 18 | RILEX ACE FORM T | 6.60 | 1.50 | 67.35 |
| 19 | RILEX ACE FORM U | 6.60 | 3.00 | 67.35 |
| 20 | RILEX ACE FORM V | 6.60 | 9.00 | 42.86 |
| 21 | RILEX ACE FORM Z | 6.60 | 15.00 | 59.18 |
| 22 | RILEX ACE FORM X | 0.66 | 1.50 | 18.37 |
| 23 | RILEX ACE FORM Y | 2.60 | 1.50 | 42.86 |
| 24 | RILEX ACE FORM W | 4.60 | 1.50 | 63.27 |
| 18 | RILEX ACE FORM T | 6.60 | 1.50 | 67.35 |
| 26 | RILEX ACE FORM AA | 8.80 | 1.50 | 74.23 |
| 27 | RILEX ACE FORM AB | 11.00 | 1.50 | 74.23 |
| 28 | RILEX ACE FORM AC | 13.20 | 1.50 | 73.47 |
| 29 | RILEX ACE FORM AD | 0.66 | 0.15 | 73.47 |
| 30 | RILEX ACE FORM AE | 2.60 | 0.35 | 0.00 |
| 31 | RILEX ACE FORM AF | 4.60 | 0.70 | 26.53 |
| 18 | RILEX ACE FORM T | 6.60 | 1.50 | 67.35 |
| 33 | RILEX ACE FORM AG | 8.80 | 3.00 | 30.61 |
| 34 | RILEX ACE FORM AH | 11.00 | 9.00 | 77.50 |
| 35 | RILEX ACE FORM AI | 13.20 | 15.00 | 77.50 |

In the tested compositions of lines 1-7 of Table 2, no silica was used for the products formulations. In this trend the defoaming activity is kept below the 30% for concentrations of simethicone lower than 9%. Upon the 9% of simethicone the defoaming activity grow until a maximum value of 70.83%.

In the tested compositions of lines 8-14 of Table 2, no simethicone was used for the product formulations. In this trend a relation between silica concentration and defoaming activity is shown. Even at the higher silica concentration level (15%) the % of the foam reduction does not go upon the value of 34.69%.

In the tested compositions of lines 15-21 of Table 2, in presence of a fixed amount of simethicone 6.6%, the defoaming activity gain the maximum value of 67.35% at the silica concentrations value of 1.5 and 3%. The other formulations show lower levels of defoaming activity.

In the tested compositions of lines 22-28 of Table 2, the correlation between the simethicone concentration and the % of foam reduction in presence of a fixed amount of silica 1.5% is shown. In this trend the defoaming activity grows proportionally to the simethicone concentration but the growth is not linear and the growth rate is slower for concentrations higher than the 6.6%. For concentrations higher than 8.8% no further increase of % of foam reduction is achieved.

In the tested compositions of lines 29-34 of Table 2, the trend of the defoaming activity of several formulations is shown at different concentrations of silica and simethicone. In this evaluation the forms T, AG, AH and AI show a range of defoaming activity from 67.35 to 77.50%. The forms AD, AE and AF show a range of activity from 0.00 to 30.61.

The invention claimed is:

1. Composition for oral use in the treatment of gastrointestinal pathologies, comprising silicone antifoaming agents and silicon dioxide in an oily solvent medium, wherein the concentration of said silicone antifoaming agents is between 0.5% and 80% by weight and comprise between 6% and 8% by weight simethicone; and the silicon dioxide in said oily solvent medium is between 1.5% and 3% by weight of the composition, wherein:
   the composition is in the form of an oily liquid composition for oral administration; and
   said oily solvent medium consists of olive oil.

2. Composition according to claim 1 comprising the following components, expressed in weight percent concentration:

| | |
|---|---|
| Olive oil | 87.880% |
| Simethicone USP | 7.500% |
| Vitamin A Palmitate 1700000 u.i | 0.120% |
| Vitamin E Acetate | 3.000% |
| Coenzyme Q10 | 0.002% |
| Micronized silica (silicon dioxide) | 1.500%. |

3. Composition according to claim 1 comprising the following components, expressed in weight percent concentration:

| | |
|---|---|
| Olive oil | 90.30% |
| Simethicone USP | 6.66% |
| Vitamin A Palmitate 1700000 u.i | 0.24% |
| Vitamin E acetate | 1.20% |
| Coenzyme Q10 | 0.10% |
| Micronized silica (silicon dioxide) | 1.500%. |

4. Composition according to claim 1, further comprising at least one further substance selected from the group consisting of enzymes, thickeners, dispersible solids (powders), prebiotic substances, immunostimulating substances, antidiarrheal substances, nutrients, substances having an inhibitory activity of microorganisms of the *Pylori* type, substances having gastroprotective activity and anti-radical agents.

5. Composition according to claim 1, further comprising at least one further substance selected from the group consisting of probiotics belonging to the families of yeasts and bacteria.

* * * * *